United States Patent [19]

Ziegler

[11] Patent Number: 4,734,276

[45] Date of Patent: Mar. 29, 1988

[54] L-LYSINE PYRUVATE AND L-HISTIDINE PYRUVATE AND THEIR USE IN THERAPY OF TISSUE AND MUCOSA DAMAGE

[75] Inventor: Walter J. Ziegler, Bettingen/Basel, Switzerland

[73] Assignee: Institut Dr. Ziegler, Basel, Switzerland

[21] Appl. No.: 789,226

[22] Filed: Oct. 18, 1985

[30] Foreign Application Priority Data

Oct. 19, 1984 [DE] Fed. Rep. of Germany ....... 3438455

[51] Int. Cl.$^4$ ................. C07D 233/54; C07D 233/64; C07D 265/00; C07C 101/00
[52] U.S. Cl. ...................................... 424/10; 548/342; 548/344; 544/63; 514/554; 514/556; 514/233; 514/234; 514/400; 260/501.11
[58] Field of Search .................. 548/342, 344; 544/63; 514/554, 556, 233, 234, 400; 260/501.11; 424/10

[56] References Cited

U.S. PATENT DOCUMENTS 3,024,272 3/1962 Hyson et al. .................. 260/501.11

Primary Examiner—Henry R. Jiles
Assistant Examiner—Robert C. Whittenbaugh
Attorney, Agent, or Firm—Armstrong, Nikaido, Marmelstein & Kubovcik

[57] ABSTRACT

The invention concerns novel pyruvate compounds namely L-lysine pyruvate and L-histidine pyruvate, the method for making these compounds by bringing together pyruvic fluid acid with L-lysine and L-histidine resp., and preparations containing L-lysine pyruvate and/or L-histidine pyruvate.

8 Claims, No Drawings

L-LYSINE PYRUVATE AND L-HISTIDINE PYRUVATE AND THEIR USE IN THERAPY OF TISSUE AND MUCOSA DAMAGE

DESCRIPTION OF THE INVENTION

The invention concerns novel derivatives of pyruvic acid: L-lysine pyruvate and L-histidine pyruvate, the making of these compounds and their use for prophylaxis or for the therapy of damages in organ tissues of the human and animal body caused by tissue damaging active substances contained in medicaments, food or other materials apt for ingestion. The tissues afflicted encompass all mucosa tissue of the alimentary and digestive tract, of the pulmonary system extending from the nose into the lung but also lips, vaginal and other tissues as well as skin epithelia of the body surface.

Many materials, in particular medicaments, food and other materials apt for ingestion that are brought to action on men or animals are exerting an undesired side-effect apart from the desired effect. Such side-effects are occurring in particular with anti-inflammatory substances such as phenyl butazone, oxyphenyl butazone and drugs for the treatment of rheumatic disorders.

With the materials or mixtures ingested by men or animals a differentiation is made between a dose-dependent noxious effect and an undesired side-effect not caused by overdosing. Accordingly antiinflammatory agents, represented for instance by acetyl salicylic acid are inducing damages on the mucosa of the gastro-intestinal tract as an undesired side-effect. Also certain derivatives of phenyl acetic acid, e.g. diclofenac sodium contained as active substance in antirheumatic drugs are exerting a cell damaging side-effect.

Since in most of the cases these drugs have to be taken for an extended period and often several times per day a considerable damage to the tissue is done by the undesired side-effects, in particular a destruction of the mucosa resulting in the development of ulcers.

From DE-OS No. 31 23 259 it is known that sodium pyruvate can be used as a mucosa protecting agent. When sodium pyruvate is administered there is the disadvantage that the protective agent contains sodium ions in considerable quantities, undesired in particular in the case of high blood pressure, and that a certain irritation of the gastric mucosa—counteracting the protective action—occurs due to the alcaline properties of sodium pyruvate. A further disadvantage is incurred inasmuch the organism is loaded with sodium ions by administration of sodium pyruvate.

The basic aim of the invention is to offer a substance not showing the disadvantages of sodium pyuvate and which is in particular more effectively applicable for the prophylaxis and therapy of tissue damages of all kind.

Unexpectedly it was found that a reduction of cell protrusions caused by agents detrimental to cells is achieved by L-lysine pyruvate, L-histidine pyruvate or a mixture thereof. These compounds are novel. They are made by bringing together pyruvic acid, preferably freshly distilled, with an aqueous solution of the L-amino acids. The reaction product thus formed is cooled and subsequently lyophilised. The molecular formula of L-lysine pyruvate is $C_9H_{18}N_2O_5$ and of L-histidine pyruvate $C_9H_{13}N_3O_5$.

The salts of pyruvic acid with the amino acids lysine and histidine are characterised by a practically neutral reaction in aqeous solution. This property is as such in the sense of a buffering activity not decisive for an increased potency in preventing formation of cell plasma polyps on the mucosa. It is, however, advantageous that the relatively neutral aqeous solutions of L-lysine pyruvate and L-histidine pyruvate do not cause irritation of the gastric mucosa.

It is surprising that the compounds according to the invention are exerting such an excellent activity against cell protrusion since lysine and histidine are not links in the metabolic citric acid cycle and since lysine and histidine are therefore not fed into the citric acid cycle such as other amino acids like alanine.

It has been found that by using L-lysine pyruvate and/or L-histidine pyruvate the cell damaging or tissue damaging side-effects as described above of many drugs, food and other ingested materials can be eliminated practically in total. The molar ratio between tissue damaging substance and the protective substances L-lysine pyruvate and/or L-histidine pyruvate is preferably 1:1-3. A good protecting activity is achieved already with a molar ratio of 1:1.

The compounds L-lysine pyruvate and/or L-histidine pyruvate according to the invention may be administered together with the tissue damaging substance, that is the drug or the food or other ingested materials as well as in separate formulations. L-lysine pyruvate and/or L-histidine pyruvate may be administered as powders, tablets, granulations, coated tablets or as solutions. The compounds according to the invention may also be administered as powders, tablets, granulates, coated tablets or solutions together with the drugs exerting the cell damaging action or mucosa damaging side-effect. The preparation administered may contain in addition other usual components such as excipients, flavours, colouring agents, coating materials and/or other auxiliary substances.

The ratio of L-lysine pyruvate and/or L-histidine pyruvate in the preparation to be administered is preferably in the range of an effective amount sufficient to prevent or to suspend virtually the tissue damaging effect caused by the tissue damaging agent in the medicament administered.

The invention is illustrated in more detail by means of the following examples:

EXAMPLE 1

Synthesis of L-Lysine pyruvate

To 0.88 g (10 mmol) freshly distilled pyruvic acid in a 100 ml laboratory glass flask a solution of 1.46 g (10 mmol) L-lysine in 10 ml. water was added dropwise with stirring; another 5 ml. water were used for rinsing. Immediately after termination of the reaction the reaction mixture was deep frozen and lyophilised subsequently. The product obtained was ground into fine flakes and after drying in high vacuum over $P_2O_5$ and KOH 2.34 g (10 mmol) lysine pyruvate were obtained. A solution of 100 mg of the preparation in 1 ml. water had a pH value 5.0.

IR spectrum (KBr): bands at 3410, 3000 (broad), 2090, 1620 (broad), 1500, 1390, 1350, 1230, 1165, 1135, 1020, 955, 930, 815, 740 and 660 cm$^{-1}$.

Molecular formula: $C_9H_{18}N_2O_5$; mol. weight: 234.25

Structural formula:

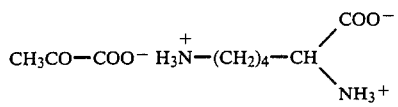

EXAMPLE 2

Synthesis of L-histidine pyruvate

The procedure according to example 1 was repeated with the difference that 1.55 g (10 mmol) 1-histidine in place of L-lysine were used. After lyophilising and drying 2.43 g (10 mmol) L-histidine pyruvate were obtained in fine flakes. A solution of 100 mg of L-histidine pyruvate in 1 m. water had a pH 4.9.

Molecular formula: $C_9H_{13}N_3O_5$, mol. weight: 243.22
Structural formula:

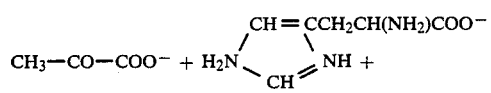

EXAMPLE 3

To investigate the effectiveness of the compounds according to the invention in preventing formation of cell protrusions experiments with rats were made whereby acetyl salicylic acid was administered as mucosa damaging substance. The extent of mucosa damage was determined by the number of cell plasma polyps formed on the gastric mucosa. The formation of cell plasma polyps, their concentration and counting was controlled in groups of 5 Sprague Dawley rats each with a body weight of 140–160 g, and the number of cell polyps was calculated on 1 g stomach (empty weight). The animals were fasted 15–17 hours before the test. The test substances, dissolved in Krebs-Ringer solution or aqua bidest. were administered by oesophageal sound. The residence time of the test substance until removal of the stomachs of a group of rats was approximately 20 up to 30 min. maximum. Thereby the cell plasma polyps, separated from the gastric mucosa, were determined dose-dependently. Five animal tests per group were made within 40 min. whereby the stomachs were worked up as follows: To each rat 4–5 ml of the solution consisting of the test substance dissolved in aqua bidest were administered. After an acting time of 15 to 20 min. the stomach was removed and dissected. The content of the stomach was collected and analysed for plasma polyps. The empty stomach was put into oxygenated Krebs-Ringer solution with added glucose and homogenised thereafter. The homogenised material was underlayed with a solution of a saccharose copolymer with epichlorohydrine and centrifuged. The layer containing the cell plasma polyps was then centrifuged at 13,000 U/min., the upper layer was discarded and the plasma polyps from the sediment were counted.

The following table shows the substances applied and the count of plasma polyps on the gastric mucosa from a series of five animals as mean value per gram of rat stomach.

| Nr. | Substances applied | Number of PP* per 1 g of rat stomach |
| --- | --- | --- |
| 1. | 4,5 ml Aq. bidest. | approx. 238 000 |
| 2. | 4,5 ml. Aq. bidest. with 0,5 mmol L-lysine pyr. | approx. 230 000 |
| 3. | 4,5 ml Aq. bidest. with 0,5 mmol ASA** | approx. 728 000 |
| 4. | 4,5 ml Aq. bidest. with 0,5 mmol ASA and 0,5 mmol L-lysine pyr. | approx. 390 000 |
| 5. | 4,5 ml Aq. bidest. with 0,5 mmol ASA and 0,5 mmol L-histidine pyr. | approx. 414 000 |

*PP = plasma polyps
**ASA = acetyl salicylic acid

The table above shows that by concomitant administration of L-lysine pyruvate or L-histidine pyruvate resp. a quite considerable reduction of plasma polyp production on or in the gastric mucosa which is caused by the cell damaging acetyl salicyclic acid is achieved. In the tests performed it has been demonstrated that the compounds according to the invention are exerting a considerably better protecting action compared to e.g. the sodium pyruvate known before.

I claim:

1. A pyruvic acid selected from the group consisting of L-lysine pyruvate and L-histidine pyruvate.

2. A composition for prohylaxis and therapy of tissue and mucosa damages comprising a pharmaceutically effective amount of a pyruvic acid derivative selected from the group consisting of L-lysine pyruvate and L-histidine pyruvate and a pharmaceutically acceptable carrier.

3. A composition as claimed in claim 2, wherein the pharmaceutically effective amount of said selected pyruvic acid derivative, is an amount that suspends the undesired side-effects of ingested materials which cause tissue or mucosa damage.

4. A composition as claimed in claim 3 wherein tissue damaging ingested materials and the L-lysine pyruvate and/or the L-histidine pyruvate are in a molar ratio of 1:1-3.

5. A composition as claimed in claim 3, 4, or 7 wherein the mucosa and tissue damaging ingested materials are one of: (i) phenylacetic acids, phenylacetic acid, (ii) acetyl salicylic acid, (iii) phenyl butazone, (iv) oxyphenyl butazone, (v) lipid-lowering drugs, (vi) vincamine and as protecting substance L-lysine pyruvate and/or L-histidine pyruvate.

6. A composition as claimed in claim 5 wherein 2-(2,6-dichloroanilino)-phenylacetic acid and L-lysine pyruvate and/or L-histidine pyruvate respectively are contained in a molar ratio of 1:1.5-2.

7. A composition as claimed in claim 3 wherein the ingested materials and the L-lysine pyruvate and/or the L-histidine pyruvate are contained in a molar ratio of 1:1.

8. A method for prophylaxis and therapy of tissue damage caused by active substances contained in medicaments, food or other ingested materials which cause tissue and mucosa damage which comprises administering a pharmaceutically effective amount of at least one of L-lysine pyruvate and L-histidine pyruvate to a patient requiring such treatment.

* * * * *